United States Patent [19]
Williams

[11] Patent Number: 4,585,653
[45] Date of Patent: Apr. 29, 1986

[54] NEURAMINIDASE TREATED ANCROD

[75] Inventor: Jeffrey W. Williams, Columbus, Ohio

[73] Assignee: Robert L. Letcher, New York, N.Y.

[21] Appl. No.: 686,232

[22] Filed: Dec. 26, 1984

Related U.S. Application Data

[63] Continuation of Ser. No. 584,102, Feb. 27, 1984, abandoned.

[51] Int. Cl.[4] .............................................. A61K 35/58

[52] U.S. Cl. .......................................... 424/98; 514/8; 514/2; 424/94; 435/68; 435/69; 435/219

[58] Field of Search .......................... 424/98, 177, 94; 435/68, 69, 219

[56] References Cited

PUBLICATIONS

Chem. Abst.-Chem. Subj. Index-10th Coll., (1977-1981), p. 45007CS.

*Primary Examiner*—Sam Rosen

*Attorney, Agent, or Firm*—Darby & Darby

[57] ABSTRACT

Disclosed is a pharmaceutically effective agent and method of use, comprising ancrod which has been incubated with neuraminidase. The neuraminidase-treated ancrod (NTA) can be substituted for ancrod in ancrod therapy, when immunological resistance to the latter has become manifest. Conversely, NTA can be administered initially, and ancrod substituted therefor after NTA resistance becomes manifest.

17 Claims, No Drawings

NEURAMINIDASE TREATED ANCROD

This is a continuation of application Ser. No. 584,102, filed Feb. 27, 1984, now abandoned.

FIELD OF THE INVENTION

This invention pertains to a method for improving the efficacy of ancrod treatment in mammals by administration of neuraminidase treated ancrod. More specifically, the invention pertains to a method of overcoming biological resistance to the administration of ancrod in mammals.

BACKGROUND OF THE INVENTION

For some years, it has been known that the venom of certain snakes, specifically pit vipers, e.g., Ankistrodon rhodostoma, contains a component which can be used as an anticoagulant. It is also known that an isolated fraction of the venom of Ankistrodon rhodostoma, hereinafter referred to as "ancrod", having a thrombin-like action functions to enzymatically degrade fibrinogen into inactive fibrinopeptides.

Fibrinogen has two important physiologic functions: (1) it is required for the formation of a stable fibrin clot, and (2) it is a primary determinant of the viscosity of plasma and, hence, blood viscosity. Degraded fibrinogen, in the form of inactive fibrinopeptides, is cleared from the circulation by the action of the reticuloendothelial system and/or the fibrinolytic system. The resultant reduction in plasma fibrinogen concentration is paralleled by an increase in fibrin degradation product (FDP) concentration. Thus, in an individual not previously exposed to ancrod, e.g., through prior treatment or snake bite, administration is accompanied by a fall in plasma fibrinogen concentration and a parallel increase in FDP concentration.

The therapeutic efficacy of ancrod arises from its ability to increase blood flow. In patients with a variety of vascular diseases, controlled reduction in fibrinogen concentration lowers the plasma viscosity and decreases the tendency of red cells to form aggregates. The overall effect is a reduction in blood viscosity and, hence, an increased blood flow, throughout the circulatory system.

It has long been known that repeated ancrod administration results in the formation of anti-ancrod substances presumably similar to antibodies) which, after approximately 45-60 days of continued therapy, achieve a sufficiently high titer to negate the beneficial effects of further ancrod administration. Clinically, the emergence of so-called "resistance" to ancrod is manifested by the return of symptoms attributable to reduced blood flow, e.g., pain, ulceration, and the like in the case of peripheral vascular disease. Biochemically, plasma fibrinogen concentration returns to pre-treatment levels and is accompanied by increased plasma and blood viscosity.

Because this ancrod resistance arises in most patients after they have received the drug for a relatively brief period, the usefulness of the drug as an effective treatment for various circulatory disorders has been severely limited.

One way of overcoming ancrod resistance is disclosed in the assignee's U.S. patent application Ser. No. 428,694, filed Sept. 30, 1982 by Letcher, now abandoned. The Letcher application discloses that resistance to ancrod can be reduced by performing plasmapheresis on the patient's blood when symptoms of ancrod resistance are observed. After plasmapheresis, effective ancrod treatment can be resumed.

It has now been unexpectedly discovered that biological resistance to ancrod therapy in mammals can be successfully overcome by treating the ancrod with neuraminidase.

DETAILED DESCRIPTION OF THE INVENTION

Ancrod is a glycoprotein, having a molecular weight of about 38,000 (mean-value). The glycoprotein comprises approximately 36% carbohydrate, about 28% of the carbohydrate is sialic acid. Ancrod enzymatically catalyzes the hydrolysis of fibrinogen, a protein normally present in blood plasma. The ancrod-catalyzed hydrolysis yields inactive fibrinopeptides. These fibrinopeptides form in filaments by end-to-end polymerization. The filaments are quickly eliminated from the circulation by the action of the reticuloen-dothelial system and/or fibrinolytic system.

Ancrod can be termed an anticoagulant because its action on fibrinogen prevents the cross linking of fibrin molecules, needed to form a blood clot. Ancrod and thrombin are alike in that both enzymes hydrolyze fibrinogen. However, only thrombin produces fibrin, a clot precursor. Ancrod's ability to cause the removal of fibrinogen from the bloodstream, rather than its disruption of the blood coagulation pathway, makes it therapeutically efficacious. If all of the patient's fibrinogen were removed from the blood, coagulation would be impossible; however, reduction to 10 or 15 percent of normal concentration causes a substantial reduction in blood viscosity and also keeps the blood coagulation pathway intact.

Before it is used to therapeutically induce hypofibrinogenaemina (low plasma fibrinogen concentration), ancrod is desireably purified and isolated from the other venom fractions. It is particularly important to remove those venom fractions containing the hemorrhagic factor. If the hemorrhagic factor is not removed from the viper venom and is administered with ancrod, toxic effects could result.

Several methods for isolating ancrod are known. Perhaps the best known method entails two separate ion-exchange chromatography procedures; see Esnouf and Tunnah, Brit. J. Haemat., 13:581-590 (1967). U.S. Pat. No. 3,743,722, issued July 3, 1973, describes a method for isolating ancrod by affinity chromatography. Agmatine-coupled agarose is used to pack the column. Agmatine (decarboxylated arginine) is a competitive inhibitor of ancrod. Ancrod is trapped in the column until almost all of the other protein materials are eluted, provided a proper sodium chloride gradient is used as the eluant. U.S. Pat. No. 3,819,605, issued June 25, 1974, describes a similar method using a modified agarose bed and eluting with a benzamidine solution. U.S. Pat. No. 3,879,369, issued on Apr. 22, 1975, describes yet another chromatographic isolation method. In this system the viper venom is placed on an agmatine-coupled agarose bed, washed with sodium chloride, and eluted with guanidine hydrochloride. Once the ancrod is purified and isolated from the viper venom it can be administered to the patient to cause therapeutic defibrination.

In patients with obliterative atherosclerotic vascular disease, plaques form on the interior surface of the larger arteries and arterioles. These obstructions reduce the flow of nutrient blood to the distal organs. Thus, for example, in one form of peripheral vascular disease, atheromatous plaques in the large arteries and arterioles of the extremities reduce blood flow below the level necessary for normal physiologic function, a condition known as ischemia. Symptomatically, this pathologic process is heralded by pain when the metabolic demands of the affected muscle cannot be met by increasing blood flow.

Ancrod treatment, possessing the ability to reduce blood viscosity and hence increase blood flow, is indicated in patients with a variety of vascular diseases. By way of non-limiting example, these diseases include moderate and severe chronic circulatory disorders of peripheral arteries, e.g., arteriosclerosis obliterans, thromboangiitis obliterans, diabetic microangiopathy and Raynaud's phenomenon; particularly in the following stages of Fontaine's classification (a scale grading the severity of peripheral vascular disease from stage I to stage V): advanced stage II (intermittent claudication with short walking distance), stage III (rest pain) and early stage IV (ulcers, small necroses). Other diseases that may be alleviated with ancrod therapy include those associated with mononuclear cell infiltration of the blood vessel walls, e. g., so-called "vasculitis". In general, any disorder of the circulatory system manifested by a fibrinogen concentration greater than 50% higher than normal can be effectively treated by the administration of ancrod.

Clinical improvement is usually evident within two weeks of continual ancrod therapy. Ancrod is administered in 0.5 to 2.5, but preferably 1.0 to 2.0, and ideally 1.5 Twyford units per kilogram of body weight per day. Potency of ancrod is assayed in vitro by comparing the abilities of ancrod and a standard solution of thrombin to clot a solution of human fibrinogen. (One Twyford unit of ancrod will clot the fibrinogen solution in the same time as does 1 NIH-unit of thrombin.) Ancrod is generally administered by subcutaneous injection on a daily basis. The drug can also be administered by intravenous injection although this route is preferably used only with hospitalized patients. Ancrod can also be administered orally if it is protected from gastric digestion. This is usually accomplished by administering the drug in a hard shell dosage form (e.g., a capsule, tablet, pill or beadlet) that is surrounded with a capsular (enteric) coating, allowing release in the intestine where the environment is less destructive to protein. Suitable enteric coating materials are well known in the art and include shellac-stearic acid-tolu balsam; cellulose acetate phthalate-tolu balsam-shellac; shellac-castor oil; ammoniated shellac cellulose acetate phthalates with or without plasticizer and dusting powder(s).

Fibrinogen concentration in normal human subjects is altered by climate and altitude changes. The concentration at sea level ranges from approximately 200 to 400 mg/dl (milligrams of fibrinogen per deciliter of plasma). The concentration range for the disease state is more variable and can have a considerably higher limit. Therefore, individual dosages should be determined for each patient, and should be adjusted to reduce fibrinogen concentration to 70-100 mg/dl. Improvement in patients with peripheral vascular disease is manifested by an improved exercise tolerance, absence of rest pain, healing of superficial skin ulcers, and the like. Recent reports allege that short term (e.g., less than 45 days) ancrod therapy can be used to prevent myocardial infarction in patients with crescendo angina because it improves blood flow in the coronary arteries.

Unfortunately, due to the antigenic nature of ancrod, repeated administration in mammals, particularly humans, results in the formation of anti-ancrod substances resembling antibodies. After approximately 45-60 days of therapy, these antibody like substances achieve a sufficiently high titer to neutralize the beneficial effects of further ancrod administration. As noted above, clinically, the emergence of ancrod resistance is manifested by the return of symptoms attributable to reduced blood flow, e.g., pain, ulceration, and the like. Biochemically, plasma fibrinogen concentration returns to pre-treatment levels and is accompanied by increased plasma and blood viscosities.

Biological resistance to ancrod is monitored indirectly by measuring the patient's plasma fibrinogen concentration. Resistance to ancrod is encountered when the patient's plasma fibrinogen concentration rises to between about 75 and 100 percent of pretreatment levels. Resistance can also be monitored by measuring the patient's plasma or blood viscosity, which varies with fibrinogen concentration. Measurement of fibrin degradation product (FDP) concentration, indicative of the activity of ancrod in hydrolysing fibrinogen, is another means for monitoring resistance.

It has now been unexpectedly discovered that resistance to prolonged ancrod therapy can be successfully prevented by administering ancrod which has been subjected to incubation with neuraminidase.

The sialic acids comprise a family of amino sugars containing 9 or more carbon atoms. The sialic acids appear to be regular components of all types of mucoproteins, mucopolysaccharides and certain mucolipids, as well as glycoproteins. See, e.g., Merck Index, 10th Edition, 1983, Ref. 8320.

Neuraminidase is an enzyme having wide distribution in micro-organisms and animal tissues Neuraminidase hydrolyses neuraminic acid residues including the sialic acid residues associated with the ancrod glycoprotein. With the exception of residues blocked by steric hindrance, neuraminidase can remove all of the susceptible residues by utilizing prolonged incubation with ancrod.

In order to illustrate the present invention, reference is made to the following examples which, however, are not intended to limit the invention in any respect.

EXAMPLE 1

Ancrod was treated with neuraminidase utilizing the following procedure. 1 0 mg. of freeze-dried type VI neuraminidase purchased from Sigma Chemical Co. was added to 77 Twyford units of ancrod obtained from Twyford Pharmaceuticals, in phosphate buffered saline, pH 6.8, so that neuraminidase content was 5% of the total protein in solution by weight. The mixture was allowed to incubate at room temperature (20° C.) for approximately 4 hours. The neuraminidase-treated ancrod (NTA) was isolated from the cleaved neurominic acid residues and neuraminidase by gel filtration chromatography using Sephadex G100, obtained from Pharmacia, in a column equilibrated with 2.5 mM phosphate buffered saline at pH 6.8. The removal of neuraminic acid residues from the NTA was verified by polyacrylamide gel electrophoresis. The NTA has a markedly reduced mobility at pH 8.2 compared with untreated ancrod. The isolated NTA was then lyophilized, redissolved in 1 ml. phosphate buffered saline, pH 6.8, and 70 Twyford units were obtained.

In order to determine the relative activity of NTA versus native ancrod the activity of both was tested against the synthetic substrate N-α-benzoyl-L-arginine ethyl ester.

EXAMPLE 2

25 ul of native ancrod (1.9 Twyford units) were added to 2 ml of 10 mM Tris buffer, pH 8.5, containing 0.625 mM synthetic substrate. The rate of increase in absorbance at 253 nm at various time intervals was measured using a Cary 219 spectrophotometer. Reaction rates measured at different enzyme concentrations verified that there is a linear relationship between enzyme concentration and the observed velocity of the reaction. 1 ml of ancrod (77 Twyford units) was mixed with 0.9 units of neuraminidase and allowed to react at room temperature (20° C.) for 4 hours. One unit of neuraminidase is defined as the amount required to liberate 1.0 uM of N-acetyl neuraminic acid per minute, at pH 5.0 and 37° C. using bovine submaxillary mucin as substrate. Aliquots of this reaction mixture were removed at time intervals listed below and the activity measured as shown below.

| TIME (MIN) | RATE (O.D./MIN) | % CONTROL ACTIVITY |
|---|---|---|
| 0 | .022 | 100 |
| 2 | .021 | 95 |
| 5 | .020 | 91 |
| 12 | .020 | 91 |
| 23 | .020 | 91 |
| 58 | .020 | 91 |
| 120 | .020 | 91 |
| 400 | .020 | 91 |

The results above show that the NTA has esterase activity almost equal to that of native ancrod.

Native ancrod and NTA were then compared for coagulant activity with human fibrinogen.

EXAMPLE 3

10 ul of ancrod (77 Twyford units/ml) were added to a 1 ml solution of human fibrinogen obtained from Pacific Hemostasis Inc., La Jolla, Calif., at 1 mg/ml in 50 mM phosphate buffered saline at pH 7.0. The mixture was then observed for the time necessary to generate a clot. The clot end point was defined as the point at which a clot was first visually detectable. Native ancrod was able to clot the fibrinogen in 21±3 seconds (95% confidence level). The procedure was repeated using NTA instead of native ancrod. The NTA clotted the fibrinogen in 23±4 seconds. These results indicate that NTA maintains essentially full fibrinolytic activity compared to native ancrod.

EXAMPLE 4

In order to determine the cross reactivity, if any, of NTA and native ancrod, an Ouchterlony immunoprecipitation assay was performed with a 1% agar plate. The central well was filled with serum from a patient currently undergoing ancrod therapy and demonstrating resistance to ancrod. In three equidistant radially placed wells (15 mm from the central well) were placed respectively: commercial ancrod, NTA, and native ancrod isolated from snake venom. As expected, the commercial ancrod and ancrod isolated from snake venom showed the characteristic crescent indicative of cross reaction between the serum from an ancrod resistant patient and the two types of ancrod. Suprisingly, the NTA region showed very little cross reactivity, indicating very little cross over reactivity between ancrod and NTA antibodies.

EXAMPLE 5

The experiment of example 4 was carried out using serum from a New Zealand White Rabbit immunized with NTA and Freund's complete adjuvant. 1 ml of NTA (1.5 mg NTA) was thoroughly mixed with 1 ml of Freund's complete adjuvant. 0.5 ml was injected intramuscularly into each hind leg and the remainder was injected subcutaneously into the back. After 4 weeks, the procedure was repeated, using Freund's incomplete adjuvant rather than complete adjuvant. The three outer wells contained commercial ancrod, NTA and ancrod isolated from snake venom, respectively. Only the NTA region showed any cross reactivity, indicating that NTA antibodies do not cross react with native ancrod.

These experiments show the potential value of the present invention in reducing clinical resistance to ancrod. The results of the cross reactivity studies indicate that it is likely that NTA administered after resistance has been established to native ancrod will be effective and not be met with resistance from ancrod antibodies. Conversely, if NTA is administered initially, native ancrod could be administered after NTA resistance becomes manifest. Alternatively, both ancrod and NTA can be administered simultaneously or concurrently.

The routes of administration for NTA are the same as those for untreated ancrod described above. NTA can be administered in the same dosage forms as native, untreated ancrod described above.

Individual dosages should be determined for each patient and should be adjusted to reduce fibrinogen concentration to 70–100 mg/dl. Typically, this is accomplished by administering between 0.5 and 2.5 Twyford units of NTA per day.

I claim:

1. A biologically effective agent comprising:
   ancrod which has been subjected to the enzymatic action of neuraminidase and is essentially free of neuraminic acid residues.
2. The agent of claim 1 provided in a hard shell dosage form.
3. The agent of claim 2 further comprising an enteric coating surrounding said hard shell dosage form.
4. The agent of claim 2 wherein said hard shell dosage form comprises a capsule.
5. The agent of claim 2 wherein said hard shell dosage form comprises a tablet.
6. The agent of claim 3 wherein said agent is free of sialic acid.
7. The agent of claim 3 having low cross-over activity with NTA antibodies.
8. The agent of claim 3 wherein said coating comprises shellac-castor oil.
9. The agent of claim 3 wherein said coating comprises ammoniated shellac cellulose acetate phthalate.
10. The agent of claim 9 wherein said coating additionally comprises a plasticizer.
11. The agent of claim 1 further comprising a suitable carrier for intravenous injection.
12. The agent of claim 1 further comprising a pharmaceutically acceptable carrier for subcutaneous injection.
13. A method of lysing fibrinogen comprising:
    lysing said fibrinogen with a biologically effective amount of ancrod having been treated with neuraminidase.

14. The method of claim 13 wherein said ancrod treated with neuraminidase is essentially free of neuraminic acid residue.

15. The method of claim 13 wherein said fibrinogen is treated with said ancrod treated with neuraminidase in vitro.

16. The method of claim 13 wherein said fibrinogen is mammalian fibrinogen.

17. The method of claim 16 wherein said fibrinogen is human fibrinogen.

* * * * *